US009955696B2

(12) United States Patent
Hemsarth et al.

(10) Patent No.: US 9,955,696 B2
(45) Date of Patent: May 1, 2018

(54) ECTOPARASITICIDAL FORMULATIONS

(71) Applicant: The Hartz Mountain Corporation, Secaucus, NJ (US)

(72) Inventors: W. Lance Hemsarth, Ringwood, NJ (US); Keith Goldman, Middletown, NJ (US); Ellen McGarvey, Bayonne, NJ (US)

(73) Assignee: THE HARTZ MOUNTAIN CORPORATION, Secaucus, NJ (US)

( * ) Notice: Subject to any disclaimer, the term of this patent is extended or adjusted under 35 U.S.C. 154(b) by 0 days. days.

(21) Appl. No.: 15/234,143

(22) Filed: Aug. 11, 2016

(65) Prior Publication Data

US 2017/0000131 A1   Jan. 5, 2017

Related U.S. Application Data

(63) Continuation of application No. 14/960,714, filed on Dec. 7, 2015, now abandoned, which is a continuation of application No. 14/602,901, filed on Jan. 22, 2015, now Pat. No. 9,247,733, which is a continuation of application No. 14/242,226, filed on Apr. 1, 2014, now Pat. No. 8,993,613, said application No. 14/602,901 is a continuation of application No. 14/242,178, filed on Apr. 1, 2014, now Pat. No. 9,049,860.

(60) Provisional application No. 61/812,905, filed on Apr. 17, 2013.

(51) Int. Cl.
| | |
|---|---|
| *A01N 53/00* | (2006.01) |
| *A01N 25/02* | (2006.01) |
| *A01N 47/02* | (2006.01) |
| *A01N 25/22* | (2006.01) |
| *A01N 25/00* | (2006.01) |
| *A01N 43/56* | (2006.01) |

(52) U.S. Cl.
CPC ............ *A01N 53/00* (2013.01); *A01N 25/00* (2013.01); *A01N 25/02* (2013.01); *A01N 25/22* (2013.01); *A01N 43/56* (2013.01); *A01N 47/02* (2013.01)

(58) Field of Classification Search
None
See application file for complete search history.

(56) References Cited

U.S. PATENT DOCUMENTS

| | | |
|---|---|---|
| 5,232,940 A | 8/1993 | Hatton et al. |
| 5,334,585 A | 8/1994 | Derian |
| 5,567,429 A | 10/1996 | Senbo |
| 5,618,945 A | 4/1997 | Casado et al. |
| 6,001,658 A | 12/1999 | Sirinyan et al. |
| 6,010,710 A | 1/2000 | Etchegaray |
| 6,045,816 A | 4/2000 | Narayanan |
| 6,066,660 A * | 5/2000 | Mizutani ............... A01N 43/56 514/359 |
| 6,090,751 A | 7/2000 | Chen |
| 6,096,329 A | 8/2000 | Jeannin |
| 6,117,854 A | 9/2000 | Silverman et al. |
| 6,395,765 B1 | 5/2002 | Etchegaray |
| 6,620,943 B1 | 9/2003 | Clavel et al. |
| 6,685,954 B2 | 2/2004 | Jeannin |
| 6,718,442 B1 | 4/2004 | Hunter et al. |
| 6,867,229 B2 | 3/2005 | Etchegaray |
| 6,881,848 B2 | 4/2005 | Clavel et al. |
| 6,962,713 B2 | 11/2005 | Huet et al. |
| 6,991,801 B2 | 1/2006 | Soll et al. |
| 6,998,131 B2 | 2/2006 | Soll et al. |
| 7,199,246 B2 | 4/2007 | Rousseau |
| 7,235,571 B2 | 6/2007 | Beckmann et al. |
| 2009/0036407 A1 | 2/2009 | Taylor |
| 2009/0069387 A1 | 3/2009 | Ecker et al. |
| 2011/0046579 A1 | 2/2011 | Derrieu et al. |
| 2012/0071484 A1 | 3/2012 | Reynolds |

FOREIGN PATENT DOCUMENTS

| | | |
|---|---|---|
| JP | 09-249502 | 9/1997 |
| WO | 88/00184 A1 | 1/1988 |
| WO | 2005/058038 | 6/2005 |
| WO | WO 2007/143298 | 12/2007 |
| WO | 2009/033175 | 3/2009 |
| WO | 2011/062299 | 5/2011 |
| WO | WO2011/062299 * | 5/2011 |

OTHER PUBLICATIONS

The International Search Report & Written Opinion mailed in the counterpart PCT/US2014/033713, ISA/US, dated Nov. 5, 2014.

(Continued)

*Primary Examiner* — Dennis Heyer
(74) *Attorney, Agent, or Firm* — Gottlieb, Rackman & Reisman, P.C.

(57) ABSTRACT

The invention provides an ectoparasiticidal formulation which comprises an ectoparasiticidal agent, preferably the pyrethroid tetramethrin, as the pesticidally-active ingredient, together with a crystallization inhibitor selected from the group consisting of alkyl-substituted pyrrolidones, and optionally, one or more organic solvents and/or co-solvents. Preferably, the crystallization inhibitor is N-octyl pyrrolidone, and the organic solvent, if present, preferably comprises diethylene glycol monoethyl ether. The ectoparasiticidal formulation surprisingly yields a significantly enhanced speed of kill. Methods for manufacturing the formulation, as well as methods for treating animals infested with ectoparasites, are also disclosed.

10 Claims, No Drawings

(56) References Cited

OTHER PUBLICATIONS

Extended Search Report, European Patent Office, co-pending Application No. 14785698.3, dated Nov. 4, 2016.
Nishiguchi, Naonobu et al., "Animal ectoparasite controlling composition", XP-002763427; retrieved from STN Database accession No. 163:226554, JP 2015 131776, Jul. 23, 2015.
Notice of Reasons for Rejection, Japanese Patent Office, co-pending Application No. 2016-508972, dated Oct. 25, 2016.
Office Action, U.S. Patent Office for counterpart U.S. Appl. No. 14/242,178, dated Jun. 2, 2014.
Office Action, U.S. Patent Office for counterpart U.S. Appl. No. 14/242,178, dated Jan. 26, 2015.
Office Action, U.S. Patent Office for counterpart U.S. Appl. No. 14/242,226, dated Aug. 22, 2014.

\* cited by examiner

ECTOPARASITICIDAL FORMULATIONS

REFERENCE TO RELATED APPLICATIONS

This application is a Continuation application of U.S. Ser. No. 14/960,714 filed Dec. 7, 2015, which is a Continuation application of Ser. No. 14/602,901 (Publication No. 2015/0157013) filed Jan. 22, 2015, which (a) is a continuation of U.S. Ser. No. 14/242,226 (U.S. Pat. No. 8,993,613) filed on Apr. 1, 2014, which in turn claims priority from Provisional Application No. 61/812,905 filed Apr. 17, 2013; and (b) is also a Continuation application of U.S. Ser. No. 14/242,178 (U.S. Pat. No. 9,049,860) filed Apr. 1, 2014, which in turn claims priority from U.S. 61/812,905 filed Apr. 17, 2013.

TECHNICAL FIELD

The present invention relates broadly to compositions and methods for treating animals infested with parasites, and in particular, to topical compositions useful for treating companion animals infested with common ectoparasites. More specifically, this invention relates to improved ectoparasiticidal compositions for treating household pets infested with fleas, to methods of using the same, and to methods for preparing the same.

BACKGROUND OF THE INVENTION

The infestation of companion animals, and in particular household pets such as dogs and cats, with ectoparasites such as fleas, ticks and the like, which live by hematophagy (i.e., by sucking the animal's blood), is highly undesirable. The prior art has developed numerous ready-to-use topical formulations and compositions for treating such infestations, many of which are "spot on" or "pour on" formulations that are applied by deposition on the animal's skin, and which contain an N-phenyl pyrazole, and in particular, 1-[2,6-$Cl_2$-4-$CF_3$-phenyl]-3-CN-4-[SO—$CF_3$]-5-$NH_2$-pyrazole, whose common name is fipronil, as the active ingredient. Fipronil is an insecticide that is particularly effective to control and/or eliminate adult fleas and ticks, and when applied topically, is acceptably safe for use on companion animals such as dogs and cats.

U.S. Pat. No. 6,395,765 to Etchegaray, which is incorporated herein by reference in its entirety, discloses and claims particular ectoparasiticidal compositions comprising (a) an N-phenyl pyrazole, such as fipronil, as the active ingredient, along with inert, inactive ingredients including (b) a crystallization inhibitor, (c) an organic solvent, and (d) an organic co-solvent. A variety of specific crystallization inhibitors, organic solvents and organic co-solvents are disclosed.

In particular, the preferred crystallization inhibitor system is described as being a combination of a film-forming agent of polymer type and a surfactant, with the film-forming agent of polymer type being most preferably exemplified by polyvinylpyrrolidone, polyvinyl alcohols, and copolymers of vinyl acetate and vinylpyrrolidone, and with the surfactant being most preferably exemplified by polyoxyethylenated sorbitan esters, and in particular, polysorbate 80. It is believed that these crystallization inhibitors act by forming a film matrix which, while possibly allowing small crystals to form, inhibits their subsequent growth.

Although pesticidal compositions that include this type of crystallization inhibitor system are effective, it has been determined that the rate at which ectoparasites such as fleas are eradicated is not optimal and can be improved by utilizing a different class of crystallization inhibitors, particularly those which are not film-forming agents of polymer type.

It is therefore the principal object of the present invention to provide ectoparasiticidal formulations for the treatment and protection of companion animals having enhanced efficacy.

It is another object of the present invention to provide ectoparasiticidal compositions that are easy to use.

It is yet a further object of the present invention to provide ectoparasiticidal formulations having a higher rate of kill of parasites than can be achieved using presently-available compositions.

SUMMARY OF THE INVENTION

These and other objects of the present invention are achieved by providing an ectoparasiticidal formulation which surprisingly yields a significantly enhanced speed of kill. The improved formulation comprises an ectoparasiticidal agent, preferably fipronil, as the pesticidally-active ingredient, together with a crystallization inhibitor selected from the group consisting of alkyl-substituted pyrrolidones, and optionally, one or more organic solvents and/or co-solvents.

The crystallization inhibitor is preferably N-octyl pyrrolidone, and it preferably comprises from 0.1% to 100% of the ectoparasiticidal composition (excluding the active ingredient). Optionally, the composition may also include one or more additional solvents, as well as one or more suitable carriers, extenders, and/or excipients.

The methods of the invention comprise methods of parasite control for companion animals by administering the improved ectoparasiticidal compositions to the skin of the animal, preferably in a topical fashion, as a spray-on, stripe on or spot-on formulation.

Thus, one aspect of the present invention generally concerns improved formulations for treating companion animals suffering from one or more ectoparasiticidal infestations. One embodiment of this aspect provides a formulation comprising an active ingredient such as fipronil combined with a crystallization inhibitor comprising N-octyl pyrrolidone.

Another aspect of the invention generally concerns improved methods for treating companion animals suffering from one or more ectoparasiticidal infestations. In one embodiment of this aspect of the invention, methods for administering an ectoparasiticidal formulation to an infested animal are provided. In another embodiment of this aspect of the invention, methods for manufacturing ectoparasiticidal formulations are provided.

It is a feature of the present invention that the compositions yield a kill rate for ectoparasites that is significantly improved as compared with the prior art compositions containing the same ectoparasiticidal agent. The kill rate is enhanced not only initially, immediately following application to the animal, but a high kill rate is also maintained for a longer period of time after the initial treatment than with prior art formulations.

DETAILED DESCRIPTION OF THE PREFERRED EMBODIMENT

The preferred and other embodiments of each aspect of the present invention will now be further described.

The present invention resides in the discovery that alkyl-substituted pyrrolidones, and in particular, N-octyl pyrrolidone, when used in an ectoparasiticidal composition in combination with the active ingredient fipronil, facilitates more rapid and sustained activity of the fipronil. Without being bound by any particular explanation, it is believed that this enhanced activity is due to the improved solubility of fipronil in N-octyl pyrrolidone, resulting in augmented availability of the active ingredient while it is present on the animal, and enhancing the ability of fipronil to penetrate the arthropod cuticle, thereby achieving, in turn, more rapid and sustained pesticidal action of the fipronil by disruption of the insect's central nervous system.

In accordance with one embodiment of the invention, the composition comprises fipronil as the pesticidally-active ingredient, in combination with the preferred crystallization inhibitor, N-octyl pyrrolidone, alone (i.e., excluding any additional solvents for the pesticidally-active ingredient). In general, the composition should contain an amount of fipronil that is between about 1% and about 20% by weight of the overall composition, and it should contain an amount of N-octyl pyrrolidone that is between about 80% and about 99% by weight of the overall composition.

In accordance with another, more preferred embodiment of the invention, the composition comprises fipronil as the pesticidally-active ingredient, in combination with the preferred crystallization inhibitor, N-octyl pyrrolidone, and at least one organic solvent. In general, this composition should contain an amount of fipronil that is between about 1% and about 20% by weight of the overall composition, and it should contain an amount of N-octyl pyrrolidone that is between about 1% and about 90% by weight of the overall composition. The organic solvent may be present in the overall composition in a percentage by weight which represents the complement of 100% of the composition, given the weight percentages of fipronil and of N-octyl pyrrolidone that have been selected.

More preferably, the composition comprises an amount of fipronil that is between about 5.0% and about 11.0% by weight of the overall composition, and an amount of N-octyl pyrrolidone that is between about 10% and about 20% by weight of the overall composition. Most preferably, the composition comprises an amount of fipronil that is about 10% by weight of the overall composition, combined with an amount of N-octyl pyrrolidone that is about 15% of the overall composition.

Although N-octyl pyrrolidone is the preferred crystallization inhibitor of the present invention, other alkyl-substituted pyrrolidones can serve as the crystallization inhibitor in other embodiments of the invention. Examples of acceptable alkyl-substituted pyrrolidones include N-methyl pyrrolidone and N-dodecyl pyrrolidone. None of these alkyl-substituted pyrrolidones is a polymer, and none of them is film-forming.

The organic solvent that is selected should have a dielectric constant of between 10 and 35, and preferably between 20 and 30. Among the organic solvents that may be used, the following are preferred: acetone, benzyl alcohol, butyl diglycol, dipropylene glycol n-butyl ether, ethanol, isopropanol, methanol, ethylene glycol monoethyl ether, ethylene glycol monomethyl ether, dipropylene glycol monoethyl ether, propylene glycol, diethylene glycol monoethyl ether, ethylene glycol, cyclic carbonates and lactones; optionally, a mixture of at least two of these solvents may be utilized. Most preferably, the organic solvent comprises diethylene glycol monoethyl ether.

Optionally, the composition may also contain an organic co-solvent, having a boiling point below 100 degrees C., and preferably below 80 degrees C., and having a dielectric constant of between 10 and 40, and preferably between 20 and 30. The organic co-solvent should be volatile, so as to act as a drying promoter, and should be miscible with water and/or with the organic solvent mentioned above. If an organic co-solvent is included, then the organic solvent and the organic co-solvent may be present in the overall composition in a weight percentage representing the complement of 100% of the composition, given the weight percentages of fipronil and of N-octyl pyrrolidone that have been selected. Further, the organic solvent may be present in the overall composition in a proportion with the organic co-solvent ranging from about 1:99 to about 99:1. Among the organic solvents that may be used, the following are preferred: ethanol, isopropanol, and methanol; optionally, more than one of these co-solvents may be utilized. Most preferably, the organic co-solvent comprises ethanol.

Optionally, the composition may also contain other additional ingredients, such as carriers, extenders, and/or excipients, one or more of which may be added for processing and/or aesthetic reasons, as will be evident to those of skill in the art. Examples of such additional ingredients include carriers or extenders such as safflower oil, corn oil, sesame oil, glycerine, glycols, esters, alcohols, cyclic carbonates, lactones and even water. Safflower oil is a particularly preferred natural carrier/extender for use with the present invention, since it also helps to solubilize the waxy and oily substances that may be present on the outer surface of the flea cuticle, thus facilitating even further the penetration of the fipronil, and thereby further enhancing the speed with which it can act on the insect's central nervous system.

In general, the compositions of the present invention may be prepared by simply mixing the constituents together. Preferably, the pesticidally-active ingredient (e.g., fipronil) is added to either a single liquid ingredient, or to a combination of two or more of the liquid ingredients. The ingredients are mixed by simple stirring until all of the fipronil has been solubilized. Thereafter, the resulting solution may be prepared for administration to a companion animal as a convenient spray-on or spot-on composition, in accordance with techniques that are well-known to those of ordinary skill in the art.

The following examples of formulations containing fipronil as the pesticidally-active ingredient and N-octyl pyrrolidone as the crystallization inhibitor are given for purposes of illustration only, and are not intended to be construed as limiting the scope of the invention in any way.

EXAMPLE 1

A Formulation I, consistent with the preferred embodiment of the invention, was prepared by mixing 74.95% by weight of diethylene glycol monoethyl ether with 15% by weight of N-octyl pyrrolidone, followed by adding 10.05% by weight of technical fipronil and mixing until the fipronil was completely dissolved.

EXAMPLE 2

A Formulation II, consistent with another embodiment of the invention, was prepared by mixing 66.95% by weight of diethylene glycol monoethyl ether with 15% by weight of N-octyl pyrrolidone, followed by adding 10.05% by weight of technical fipronil and mixing until the fipronil was completely dissolved. Thereafter, enough ethanol was added to make up 8% by weight of the overall composition, followed by further mixing to complete the formula.

EXAMPLE 3

A Formulation III, consistent with yet another embodiment of the invention, was prepared by mixing 72.95% by weight of diethylene glycol monoethyl ether with 15% by weight of N-octyl pyrrolidone, followed by adding 10.05% by weight of technical fipronil and mixing until the fipronil was completely dissolved. Thereafter, enough safflower oil was added to make up 2% by weight of the overall composition, followed by further mixing to complete the formula.

In-vivo experimental speed of kill test data, which demonstrate the efficacy of the present invention, as compared with two presently available commercial ectoparasiticidal products, both of which contain fipronil as the pesticidally-active ingredient, are set forth below in Table 1.

Testing was performed on four groups of animals, consisting of eight dogs in each group; weights of the dogs ranged from 9.3 to 48.1 lbs. One group remained untreated as a control, while each of the other three groups of dogs was assigned for treatment with one of three test products.

The test products evaluated included the product commercially available under the trademark Pet Armor®, the product commercially available under the trademark Frontline Top Spot®, and the preferred composition of the present invention (using Formulation I prepared in accordance with the foregoing Example 1). All three of these test products contained 9.7% pure fipronil.

On Test day 0, the test products were applied to the test dogs in the three groups designated for treatment using the following dosages: dogs weighing up to 22 lbs received a 0.67 ml dose, dogs weighing 23-44 lbs received a 1.34 ml dose, and dogs weighing 45-88 lbs received a 2.68 ml dose. The Pet Armor® and Frontline Top Spot® test products were applied using a spot treatment, as per commercial label instructions, while test product comprising the preferred composition of the present invention was applied using the stripe treatment which is specified on the commercial label instructions of the Frontline Top Spot® test product as an acceptable alternative method of application.

One hundred (100) fleas were placed on each test dog 48 hours after application of the test product; the fleas were placed at a location away from the test product application site. After two hours of flea exposure, the test dogs were combed to remove all fleas and to record the number of fleas, both alive and dead. The percent flea reduction (% RED.) was calculated based on the test dog flea counts from the treated dogs vs the flea counts from the untreated dogs.

Weekly thereafter, the test dogs were re-infested with fleas, and then alive fleas were counted after two hours of flea exposure. The percent flea reduction was recorded through four weeks subsequent to application of the test product.

TABLE 1

| Day | Formulation I % RED.Fleas | Pet Armour7 % RED.Fleas | Frontline7 % RED. Fleas |
|---|---|---|---|
| Day 0: Treatment | | | |
| Day 2: Flea Count | | | |
| 2 hour exposure | 94 | 78 | 87 |
| Day 9: Flea Count | | | |
| 2 hour exposure | 96 | 74 | 81 |
| Day 16: Flea Count | | | |
| 2 hour exposure | 93 | 75 | 71 |
| Day 23: Flea Count | | | |
| 2 hour exposure | 91 | 62 | 69 |
| Day 30: Flea Count | | | |
| 2 hour exposure | 61 | 30 | 3 |

The data shown in Table 1 indicate that the percentage kill of fleas obtained with the present invention over a four week period of time greatly exceeds that obtained in the same amount of time with the two commercially-available fipronil-containing ectoparasiticidal products. In particular, the formulation of the present invention not only provides a high kill rate immediately following treatment, but it also maintains a kill rate that is greater than 90% for three weeks following the initial treatment, which is not achieved by the prior art formulations.

Although fipronil is preferred as the pesticidally-active ingredient, it is to be understood that alkyl-substituted pyrrolidones, and in particular, N-octyl pyrrolidone, may be utilized as a crystallization inhibitor in combination with other pesticidal ingredients that are known to be active against ectoparasites, such as other N-phenyl pyrazoles (e.g., acetoprole, ethiprole, flufiprole, pyrafluprole, pyriprole, pyrolan, vaniliprole), natural pyrethrins, synthetic pyrethroids (e.g., permethrin, etofenprox, phenothrin, flumethrin, tetramethrin), insect growth regulators (e.g., methoprene, pyriproxifen, dimilin, novaluron, lufneuron, etoxazole), synergists (e.g., PBO, n-octyl bicydoheptene dicarboximide), organophosphates, carbamates, diamides (excluding specifically chlorantraniliprole and cyantraniliprole), oxadiazines (e.g., indoxacarb), macrocyclic lactones (e.g., avermectins), formamidines (e.g., amitraz), biopesticides and botanical extracts, so as to deter their re-crystallization and thereby enhance their speed of kill as well. Compositions comprising an alkyl-substituted pyrrolidone together with one or more of these other pesticidally-active ingredients may further include, if necessary or desirable, suitable stabilizers such as, for example, butyl hydroxytoluene (BHT). However, neonicotinoids (e.g., imidacloprid, thiacloprid, dinotefuan, thiamethoxam) is a class of pesticidally-active ingredients that, even though known to be active against ectoparasites, are specifically excluded from the scope of the present invention.

While there has been described what are at present considered to be the preferred embodiments of the present invention, it will be apparent to those skilled in the art that the embodiments described herein are by way of illustration and not of limitation. Various modifications of the disclosed embodiments, as well as alternative embodiments of the invention, will become apparent to persons skilled in the art upon reference to the description of the invention. Therefore, it is to be understood that various changes and modifications may be made in the embodiments disclosed herein without departing from the true spirit and scope of the present invention, as set forth in the appended claims, and it is contemplated that the appended claims will cover any such modifications or embodiments.

The invention claimed is:

1. A method of treating an ectoparasiticidal infestation on an animal, the method comprising topically administering to the animal a ready-to-use composition by deposition of the composition on the animal's skin, the composition comprising:

(a) the pyrethroid tetramethrin in an amount from about 1% to about 20% by weight of the overall composition, (b) N-octyl pyrrolidone as a crystallization inhibitor in an amount from about 1% to about 90% by weight of the overall composition, and (b) at least one organic solvent, wherein said composition excludes neonicotinoids, chlorantraniliprole and cyantraniliprole.

2. The method of claim 1, wherein the pyrethroid tetramethrin is present in an amount from about 7% to about 11% by weight of the overall composition, and wherein said crystallization inhibitor is present in an amount from about 10% to about 20% by weight of the overall composition.

3. The method of claim 1, wherein said at least one organic solvent is selected from the group consisting of acetone, benzyl alcohol, butyl diglycol, dipropylene glycol n-butyl ether, ethanol, isopropanol, methanol, ethylene glycol monoethyl ether, ethylene glycol monomethyl ether, dipropylene glycol monoethyl ether, propylene glycol, diethylene glycol monoethyl ether, ethylene glycol, cyclic carbonates, lactones, and mixtures of at least two of said solvents.

4. A method of treating an ectoparasiticidal infestation on an animal, the method comprising topically administering to the animal a ready-to-use composition by deposition of the composition on the animal's skin, the composition comprising (a) the pyrethroid tetramethrin in an amount from about 1.0% to about 20% by weight of the overall composition, (b) N-octyl pyrrolidone in an amount from about 1% to about 90% by weight of the overall composition, and (c) at least one organic solvent.

5. The method of claim 4, wherein said at least one organic solvent comprises diethylene glycol monoethyl ether.

6. The method of claim 4, wherein the pyrethroid tetramethrin is present in an amount from about 7.0% to about 11.0% by weight of the overall composition, and wherein N-octyl pyrrolidone is present in an amount from about 10% to about 20% by weight of the overall composition.

7. The method of claim 4, wherein said at least one organic solvent is selected from the group consisting of acetone, benzyl alcohol, butyl diglycol, dipropylene glycol n-butyl ether, ethanol, isopropanol, methanol, ethylene glycol monoethyl ether, ethylene glycol monomethyl ether, dipropylene glycol monoethyl ether, propylene glycol, diethylene glycol monoethyl ether, ethylene glycol, cyclic carbonates, lactones, and mixtures of at least two of said solvents.

8. A method of treating an ectoparasiticidal infestation on an animal, the method comprising topically administering to the animal a ready-to-use composition by deposition of the composition on the animal's skin, the composition comprising (a) tetramethrin in an amount between about 1% and 20% by weight of the overall composition, (b) a crystallization inhibitor selected from the group consisting of N-methyl pyrrolidone, N-octyl pyrrolidone and N-dodecyl pyrrolidone in an amount between about 1% and 90% by weight of he overall composition, and (c) at least one organic solvent.

9. The method of claim 8 wherein said at least one organic solvent is diethylene glycol monoethyl ether.

10. The method of claim 8, wherein said at least one organic solvent is selected from the group consisting of acetone, benzyl alcohol, butyl diglycol, dipropylene glycol n-butyl ether, ethanol, isopropanol, methanol, ethylene glycol monoethyl ether, ethylene glycol monomethyl ether, dipropylene glycol monoethyl ether, propylene glycol, diethylene glycol monoethyl ether, ethylene glycol, cyclic carbonates, lactones, and mixtures of at least two of said solvents.

\* \* \* \* \*